(12) United States Patent
Chen et al.

(10) Patent No.: US 7,763,281 B2
(45) Date of Patent: Jul. 27, 2010

(54) ANTIHYPERTENSIVE PEPTIDE AND USE THEREOF

(75) Inventors: Hsiao-Ling Chen, Changhua (TW); Chuan-Mu Chen, Taichung (TW)

(73) Assignees: Da-Yeh University, Dacun, Changhua (TW); National Chung Hsing University, Taichung (TW)

( * ) Notice: Subject to any disclaimer, the term of this patent is extended or adjusted under 35 U.S.C. 154(b) by 240 days.

(21) Appl. No.: 11/856,262

(22) Filed: Sep. 17, 2007

(65) Prior Publication Data

US 2009/0075896 A1    Mar. 19, 2009

(51) Int. Cl.
*A61K 35/20* (2006.01)
*A61K 38/00* (2006.01)
*A01N 37/18* (2006.01)
*C07K 5/00* (2006.01)

(52) U.S. Cl. .............................. 424/535; 514/13; 514/2; 530/326; 530/324; 530/300

(58) Field of Classification Search ........................ None
See application file for complete search history.

(56) References Cited

U.S. PATENT DOCUMENTS 5,843,705 A * 12/1998 DiTullio et al. ................. 800/7
6,500,798 B1 * 12/2002 Stanton et al. ................. 514/2

OTHER PUBLICATIONS

Clare and Swaisgood, 2000, *J. Dairy Sci.* 83: 1187-1195.
FitzGerald et al., 2004, *J. Nutr.* 134: 980S-988S.
Kearney et al., 2005, *Lancet.* 365:217-223.
Li et al., 2004, *Nutr. Res.* 24: 469-486.
Maeno et al., 1996, *J. Dairy Sci.* 79: 1316-1321.
Minervini et al., 2003, *Appl. Environ. Microbiol.* 69: 5297-5305.
Nakamura et al., 1995, *J. Dairy Sci.* 78: 777-783.
Nakamura et al., 1995, *J. Dairy Sci.* 78: 1253-1257.
Pihlanto-Leppälä et al. 1998, *Int. Dairy J.* 8: 325-331.
Quirós et al., 2005, *J. Dairy Sci.* 88: 3480-3487.
Robert et al., 2004, *J. Agric. Food Chem.* 52: 6923-6931.
Yamamoto et al., 1994, *J. Dairy Sci.* 77: 917-922.
Yamamoto, 1997, *Biopoly.* 43: 129-134.
Yamamoto and Takano, 1999, *Nahrung* 43: 159-164.

* cited by examiner

*Primary Examiner*—Gary B. Nickol
*Assistant Examiner*—Shulamith H Shafer
(74) *Attorney, Agent, or Firm*—Occhiuti Rohlicek & Tsao LLP

(57) ABSTRACT

The present invention provides a novel antihypertensive peptide. Also provided are pharmaceutical and food compositions containing the antihypertensive peptide for treating hypertension or cardiovascular disease.

11 Claims, 9 Drawing Sheets

```
                        SEQUENCE LISTING

<160> NUMBER OF SEQ ID NOS: 9

<210> SEQ ID NO 1
<211> LENGTH: 19
<212> TYPE: PRT
<213> ORGANISM: Artificial
<220> FEATURE:
<223> OTHER INFORMATION: Synthetic peptide

<400> SEQUENCE: 1

Val Leu Ser Leu Ser Gln Pro Lys Val Leu Pro Val Pro Gln Lys Ala
1               5                   10                  15

Val Pro Gln

<210> SEQ ID NO 2
<211> LENGTH: 3
<212> TYPE: PRT
<213> ORGANISM: Artificial
<220> FEATURE:
<223> OTHER INFORMATION: Peptide derived from casein

<400> SEQUENCE: 2

Val Pro Pro
1

<210> SEQ ID NO 3
<211> LENGTH: 6
<212> TYPE: PRT
<213> ORGANISM: Artificial
<220> FEATURE:
<223> OTHER INFORMATION: Peptide derived from casein

<400> SEQUENCE: 3

Lys Val Leu Pro Val Pro
```

-continued

```
<210> SEQ ID NO 4
<211> LENGTH: 7
<212> TYPE: PRT
<213> ORGANISM: Artificial
<220> FEATURE:
<223> OTHER INFORMATION: Peptide derived from casein

<400> SEQUENCE: 4

Lys Val Leu Pro Val Pro Gln
1               5

<210> SEQ ID NO 5
<211> LENGTH: 4
<212> TYPE: PRT
<213> ORGANISM: Artificial
<220> FEATURE:
<223> OTHER INFORMATION: Pepsin-digested fragment of SEQ ID NO: 1

<400> SEQUENCE: 5

Ala Val Pro Gln
1

<210> SEQ ID NO 6
<211> LENGTH: 7
<212> TYPE: PRT
<213> ORGANISM: Artificial
<220> FEATURE:
<223> OTHER INFORMATION: Pepsin-digested fragment of SEQ ID NO: 1

<400> SEQUENCE: 6

Val Leu Pro Val Pro Gln Lys
1               5

<210> SEQ ID NO 7
<211> LENGTH: 8
<212> TYPE: PRT
<213> ORGANISM: Artificial
<220> FEATURE:
<223> OTHER INFORMATION: Pepsin-digested fragment of SEQ ID NO: 1

<400> SEQUENCE: 7

Val Leu Ser Leu Ser Gln Pro Lys
1               5

<210> SEQ ID NO 8
<211> LENGTH: 11
<212> TYPE: PRT
<213> ORGANISM: Artificial
<220> FEATURE:
<223> OTHER INFORMATION: Pepsin-digested fragment of SEQ ID NO: 1

<400> SEQUENCE: 8

Val Leu Pro Val Pro Gln Lys Ala Val Pro Gln
1               5                   10

<210> SEQ ID NO 9
<211> LENGTH: 15
<212> TYPE: PRT
<213> ORGANISM: Artificial
<220> FEATURE:
```

-continued

```
<223> OTHER INFORMATION: Pepsin-digested fragment of SEQ ID NO: 1

<400> SEQUENCE: 9

Val Leu Ser Leu Ser Gln Pro Lys Val Leu Pro Val Pro Gln Lys
1               5                   10                  15
```

ANTIHYPERTENSIVE PEPTIDE AND USE THEREOF

FIELD OF THE INVENTION

The present invention pertains to antihypertensive peptides.

BACKGROUND OF THE INVENTION

Hypertension, which affected around 26.4% of the global adult population in 2000 and was projected to affect 29.2% by 2025 (Kearney et al., 2005, *Lancet.* 365:217-223), is the major controllable risk factor associated with cardiovascular disease (CVD) events such as myocardial infraction, stroke, heart failure, and end-stage diabetes. A 5-mmHg reduction in blood pressure has been equated with around 16% reduction in CVD (FitzGerald et al., 2004, *J. Nutr.* 134: 980S-988S). The seventh Joint National Committee (JNC 7) reported the risk of heart disease and stroke increases at blood pressure above systolic blood pressure (SBP)/diastolic blood pressure (DBP) values of 115/75 mmHg. JNC 7 recommended that the pre-hypertensive individuals (SBP 120-139 mmHg or DBP 80-89 mmHg) adopt health-promoting lifestyle modifications to prevent the progressive rise in blood pressure and CVD. Therefore, the awareness of and demand for functional food ingredients or nutraceuticals for controlling blood pressure have been raised globally.

Many bioactive peptides derived from milk proteins have been found to have health-enhancing nutraceutical potential. These peptides directly influence numerous biological processes, exhibiting antimicrobial, antithrombotic, immunomodulatory, mineral carrier, opioid-like, or angiotensin I-converting enzyme (ACE) inhibitory activities (Clare and Swaisgood, 2000, *J. Dairy Sci.* 83: 1187-1195). Among the bioactive peptides, ACE inhibitory peptides have attracted particular attention and have been studied most comprehensively for their applications to prevent hypertension, an independent risk factor for CVD (Li et al., 2004, *Nutr. Res.* 24: 469-486). ACE is a multifunctional ectoenzyme located in different tissues and plays a key physiological role in renin-angiotesin, kallikrein-kinin, and immune systems. The enzyme is responsible for the increase in blood pressure by converting angiotensin-I to the potent vasoconstrictor, angiotensin-II, and by degrading bradykinin, a vasodilatory peptide, and enkephalins. Inhibition of ACE is considered to be a useful therapeutic approach in the treatment of hypertension. To date, several adverse side effects such as hypotension, increased potassium levels, reduced renal function, cough, angioedema, skin rashes, and fetal abnormalities have been associated with the ACE inhibitory drugs. However, the ACE inhibitory peptides naturally derived from food protein sources are considered to be milder and safer without the side effects associated with the drugs.

In the development of novel functional food for controlling pressure, many ACE inhibitory peptides derived from milk proteins have been found (Yamamoto et al., 1994, *J. Dairy Sci.* 77: 917-922; Maeno et al., 1996, *J. Dairy Sci.* 79: 1316-1321; Yamamoto, 1997, *Biopoly.* 43: 129-134; Pihlanto-Leppälä et al. 1998, *Int. Dairy J.* 8: 325-331; Yamamoto and Takano, 1999, *Nahrung* 43: 159-164; Clare and Swaisgood, 2000, ut supra; Minervini et al., 2003, *Appl. Environ. Microbiol.* 69: 5297-5305; Li et al., 2004, ut supra; Robert et al., 2004, *J. Agric. Food Chem.* 52: 6923-6931; and Quirós et al., 2005, *J. Dairy Sci.* 88: 3480-3487). However, most of these peptides have not yet been confirmed in vivo. Only some of the ACE inhibitory peptides have been shown to exhibit antihypertensive activities in spontaneously hypertensive rats (SHRs) (FitzGerald et al., 2004, ut supra). To date, there are several products, such as Calpis sour milk drink (Calpis Co., Japan) and C 12 peptide (DMV International, The Netherlands), on the market in the form of fermented milk or milk protein hydrolysates. In these cases, the active antihypertensive peptides including IPP, VPP, and FFVAPFEVFGK have been identified. However, there is still a great demand for antihypertensive peptides that may be administered orally in a minor dosage.

BRIEF SUMMARY OF THE INVENTION

The aim of the present invention is to provide a novel antihypertensive peptide with significant blood pressure-reducing effect in vivo. This novel peptide, whether derived from a naturally occurring protein or prepared by chemical synthesis/recombinant technology, can be included in food preparations, nutraceutical preparations, and pharmaceutical preparations for controlling blood pressure or reducing the risk of CVD.

Accordingly, the present invention features an isolated antihypertensive peptide, such as a peptide named herein as "Anti-hypertension Peptide 1" ("AP1"). As an example, AP1 has the amino acid sequence of Val-Leu-Ser-Leu-Ser-Gln-Pro-Lys-Val-Leu-Pro-Val-Pro-Gln-Lys-Ala-Val-Pro-Gln (SEQ ID NO: 1). The term "isolated" herein, as used in "isolated antihypertensive peptide," refers to an attribute of the peptide, i.e., substantially free from its naturally associated molecules. The term "peptide" used herein refers to a short polymer of amino acids (i.e., 50 or less), which are linked one by one via the peptide bond.

The present invention also features a pharmaceutical composition that contains the isolated antihypertensive peptide mentioned above and a pharmaceutically acceptable carrier. This pharmaceutical composition can be administered orally.

This invention further features a food preparation containing an antihypertensive peptide, e.g., AP1. An example of such a food preparation is a fermented dairy product.

In another aspect, the present invention features a method for treating hypertension or CVD by administering (e.g., orally) to a subject in need of this treatment an effective amount of a composition containing the just-mentioned antihypertensive peptide.

As used herein, the term "treating" refers to administering a composition containing an antihypertensive peptide to a subject that has either hypertension or CVD, or has a symptom of either disease, or has a predisposition toward either disease, with the purpose to cure, heal, alleviate, relieve, alter, remedy, ameliorate, improve, or affect either disease, the symptoms of either disease, or the predisposition toward either disease. The term "an effective amount" refers to the amount of the antihypertensive peptide that is required to confer the intended therapeutic effect in the subject. Effective amounts may vary, as recognized by those skilled in the art, depending on route of administration, excipient usage, and the possibility of co-usage with other agents.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
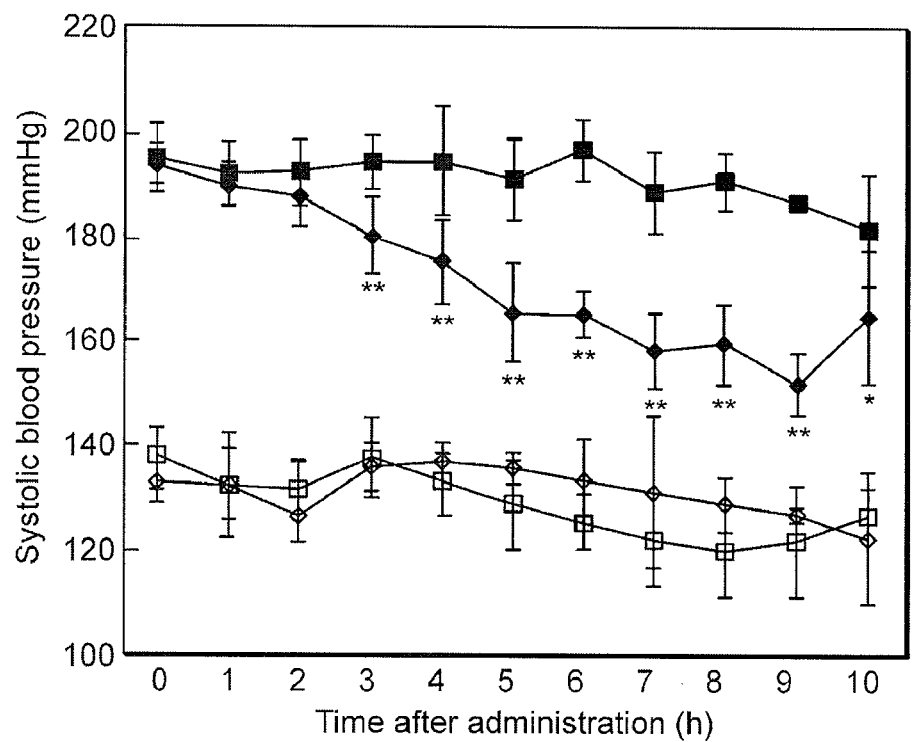
FIG. 1 is a diagram showing the change of SBP in SHRs and WKYs measured during the first 10 h after a single oral administration of supernatant powder of the fermented dairy product obtained in Example 1. The treatment groups were SHRs (n=9, ♦) or WKYs (n=6, ◊) fed with a dose of 35 mg/kg BW of supernatant powder of the fermented dairy product. The control groups were SHRs (n=6, ■) or WKYs (n=6, □) fed with a dose of 35 mg/kg BW of supernatant powder of milk. Data are shown as mean±S.E. Asterisks indicate the level of significant difference from the control in SHRs at each time interval: * indicating $P<0.05$ and ** indicating $P<0.01$.

The following abbreviations are used throughout the present invention:
ACE, angiotensin I-converting enzyme;
CVD, cardiovascular disease;
DBP, diastolic blood pressure;
SBP, systolic blood pressure;
SHR, spontaneously hypertensive rat;
WKY, Wistar-Kyoto rat;
HPLC, High Performance Liquid Chromatography; and
AP1, Anti-hypertension Peptide 1

The present invention provides an antihypertensive peptide including the amino acid sequence of Anti-hypertension Peptide 1 (AP1). The term "Anti-hypertension Peptide 1" or "AP1" refers to a peptide having the amino acid sequence of SEQ ID NO: 1 or a structural/functional variant thereof. The term "structural/functional variant" refers to a peptide having a sequence identity at least 75% (e.g., 80%, 85%, 90%, or 95%) to SEQ ID NO: 1 and possessing the antihypertensive activity. This variant can be made by introducing mutations in SEQ ID NO:1, e.g., at positions not essential to the antihypertensive activity. As SEQ ID NO:1 includes only 19 amino acid residues, it is easy to identify the amino acid residues that are essential or non-essential to the antihypertensive activity by methods well known in the art, e.g., site-mutation analysis. Moreover, conservative amino acid substitutions, i.e., replacing one amino acid residue with another having similar chemical properties, is unlikely to affect the activity of a peptide. Such mutations is also expected to preserve the anti-hypertensive activity of any structural variants of SEQ ID NO:1 thus made. The antihypertensive activity of a structural variant of SEQ ID NO:1 can be determined by assays described in, e.g., Example 1 below.

The peptide of the invention can be isolated from a natural source, such as fermented dairy products, produced by the expression of a recombinant nucleic acid molecule, or can be chemically synthesized.

To obtain the fermented dairy product of the present invention, fermentation can be conducted with one or more of the following microorganisms: lactic acid bacteria, such as those of genus *Lactobacillus, Lactococcus, Streptococcus, Leuconostoc*, and *Bifidobacterium*; and yeast, such as genus *Saccharomyces, Candida, Kluyveromyces*, and *Pichia*. Pasteurized whole or defatted mammalian milk, whey, or casein may be used as milk protein-based fermentation substrates. The fermentation temperature is preferably between 15 and 45° C., and fermentation time is preferably between 8 and 180 h. The fermented dairy products containing the antihypertensive peptide of the present invention, or functional variant thereof may be directly used as material for manufacturing functional foods or nutraceuticals.

Milk for preparing the fermented dairy product described above can be obtained from a wild-type cow, goat, sheep, pig, or horse, i.e., expressing wild-type β-casein. It also can be obtained from a genetically engineered cow, goat, sheep, horse, pig or horse, i.e., expressing modified β-casein such that through fermentation a structural/functional variant of SEQ ID NO:1 is produced.

The antihypertensive peptide of the present invention can also be produced by traditional methods of enzymatic hydrolysis of milk protein-based material, or by way of conventional organochemical synthetic methods. These methods are well known in the art and can be practiced by persons of ordinary skills in the art without undue experimentation.

Due to its excellent antihypertensive activity in vivo, the peptide of the present invention, or functional variant thereof can be used as an active ingredient in pharmaceutical compositions for preventing or treating hypertension and/or CVD.

When the antihypertensive peptide of the present invention is produced by fermentation or enzymatic hydrolysis, the fermented dairy product comprising the antihypertensive peptide or functional variant thereof may be directly employed as the active ingredient of the pharmaceutical composition. However, it may also be purified by column chromatography or any of a variety of biochemical methods to eliminate some or all components other than the antihypertensive peptide.

The pharmaceutical composition of the present invention can be manufactured by conventionally known methods with one or more pharmaceutically acceptable carriers. The term "pharmaceutically acceptable carrier" as used herein encompasses any of the standard pharmaceutical carriers. Such carriers may include, but are not limited to: saline, buffered saline, dextrose, water, glycerol, ethanol and combinations thereof.

The pharmaceutical composition of the present invention may be constituted into any form suitable for the mode of administration selected. For example, compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In addition to standard carriers, an oral pharmaceutical composition of the present invention may be supplemented with one or more excipients that are normally employed in oral formulations, such as surfactants, solubilizers, stabilizers, emulsifiers, thickeners, coloring agents, sweetening agents, flavoring agents, and preservatives. Such excipients are well known to those skilled in the art.

In an embodiment of the present invention, the pharmaceutical composition is a food preparation comprising the antihypertensive peptide of the present invention, or functional variant thereof at an amount effective for reducing blood pressure. Examples of the food preparation include but not limited to fermented dairy products, soft drinks, sport drinks, elder food, candies, and gum.

The present invention also provides a method for reducing blood pressure in a subject, said method comprising administering to the subject the antihypertensive peptide of the present invention, or functional variant thereof at an amount effective for reducing blood pressure.

In another embodiment, the present invention provides a method for prophylactic or therapeutic treatment of CVD in a subject, said method comprising administering to the subject the antihypertensive peptide of the present invention, or functional variant thereof at an amount effective for reducing blood pressure.

In the method of the present invention, the actual amount of the peptide to be administered can vary in accordance with the age, size, and condition of the subject to be treated, depending on the discretion of medical professionals.

The present invention is further illustrated by the following examples, which are provided for the purpose of demonstration rather than limitation.

Example 1

Preparation of Fermented Dairy Product and Confirmation of the Antihypertensive Activity Thereof To prepare the fermented dairy product, 100 g of defatted skim milk powder were dissolved in 900 g of ddH$_2$O. The obtained skim milk solution was pasteurized at 63° C. for 30 min, then cooled for inoculation. A 2% starter containing 10$^8$ CFU/mL bacteria identified from kefir grain including *Lactobacillus acidophilus, Lactobacillus helveticus* and *Saccharomyces cerevisiae* was added to the pasteurized skim milk. The cultivation temperature and time are 38° C. and 20 h. The fermented dairy product (1 L) was centrifuged at 12,000×g for 10 min, and the supernatants were freeze-dried and kept at −20° C. until use. Both the supernatant and the freeze-dried powder of the supernatant were enriched with antihypertensive peptides, and the amount of the peptides were determined to be 50 to 500 mg/L supernatant and 1.5-15 mg/g supernatant powder, respectively, depending on the fermentation condition (data not shown).

The inhibitory potencies of peptides on ACE activity do not always correlate with their antihypertensive effects, because some peptides with potent ACE inhibitory activities in vitro are inactive after oral administration. Therefore, the antihypertensive activity of the aforementioned supernatant powder of the fermented dairy product were measured in SHRs and normotensive rats (Wistar-Kyoto rats, WKYs) to evaluate its potential applications to functional food for preventing hypertension. The male SHRs and male WKYs used in the present and following examples were purchased from National Laboratory Animal Center (Taipei, Taiwan) and fed with laboratory chow (Rodent laboratory chow 5001, Purina Co., USA). Blood pressures including SBP and DBP of 8- to 18-wk-old SHRs (body weight, 330-360 g) and 8- to 18-wk-old WKYs (body weight, 350-380 g) were measured by the tail-cuff method employing a tail-cuff detection system (Softron BP16; Softron, Tokyo, Japan). The antihypertensive activities of the test samples were evaluated by measuring the changes in SBP and DBP of SHRs and WKYs during 0-10 h after oral administration of respective samples.

Figure 2:
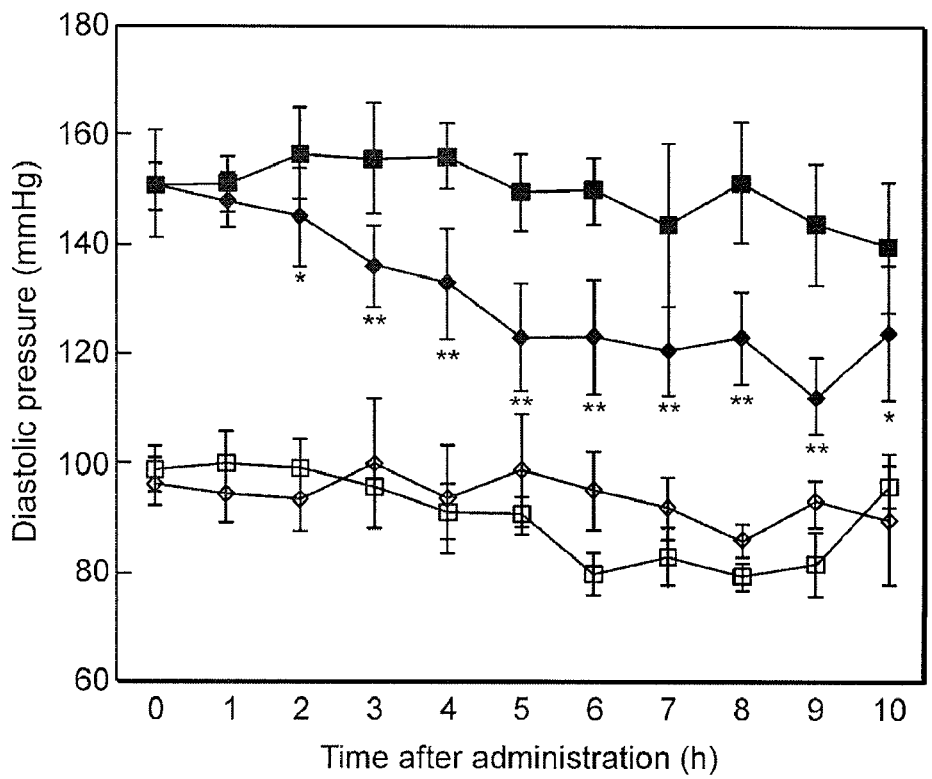
FIG. 2 is a diagram showing the change of DBP in SHRs and WKYs measured during the first 10 h after a single oral administration of supernatant powder of the fermented dairy product obtained in Example 1. The treatment groups were SHRs (n=9, ♦) or WKYs (n=6, ◊) fed with a dose of 35 mg/kg BW of supernatant powder of the fermented dairy product. The control groups were SHRs (n=6, ■) or WKYs (n=6, □) fed with a dose of 35 mg/kg BW of supernatant powder of milk. Data are shown as mean±S.E. Asterisks indicate the level of significant difference from the control in SHRs at each time interval: * indicating $P<0.05$ and ** indicating $P<0.01$.

The results of SBP and DBP observed during the first 10 h after a single oral administration with a dose of 35 mg/kg BW supernatant powder of the fermented dairy product (the treatment groups) or with the same dose of supernatant powder of ordinary milk (the control groups) are shown in FIG. 1 and FIG. 2. In SHRs fed with supernatant powder of the fermented dairy product, the mean SBP was 194.3±3.9 mmHg before administration and significantly decreased between 3 and 10 h after administration compared with the control groups (at 3, 4, 5, 6, 7, 8, 9 h, P<0.01; at 10 h, P<0.05). As to DBP, the mean value was 150.6±4.3 mmHg before administration and significantly decreased between 2 and 10 h after administration (at 2 h, P<0.05; at 3, 4, 5, 6, 7, 8, 9 h, P<0.01; at 10 h, P<0.05). The maximal decrease of SBP and DBP was 42.2±2.9 mmHg and 37.3±3.1 mmHg, respectively, observed at 9 h after administration. In WKYs, neither SBP nor DBP was significantly different between the treatment groups and the control groups. These data suggest that the supernatant powder of the fermented dairy product exhibits an antihypertensive effect only in subjects with hypertension.

Example 2

Fractionation of the Supernatant of Fermented Dairy Product and Confirmation of the Antihypertensive Activity of "Fraction A"

The aforementioned supernatant powder was re-dissolved in ddH2O, and the resulting solution was subjected to fractionation. One milliliter of the re-dissolved solution (total peptide conc. 20 mg/mL) was subjected to reverse-phase HPLC (RP-HPLC) (UV-VIS detector L-7420; Pump L-7100, Hitachi Ltd., Japan) with RP-C18 column (Vydac® HPLC Column, and Solvent A (1% trifluoroacetic acid in acetonitrile) and solvent B (ddH2O) were used as mobile phase. The peptides were eluted by a gradient from 100% solvent B to 10% solvent B during 0-10 min, 10% solvent B to 30% solvent B during 10-120 min, then 30% solvent B to 100% solvent B during 120-150 min at a flow rate of 1 mL/min. The absorbance was detected at 215 nm. The fractions were collected by min and used for the following measurement of ACE inhibitory activity.

ACE inhibitory activity was assayed by the method of Cushman and Cheung as described in *Biochem. Pharmacol.* 20: 1637-1648 (1971). The method is based on the liberation of hippuric acid from hippuryl-L-histidyl-L-leucine, catalyzed by ACE. Briefly, 30 μL of each sample solution was added to 200 μL of 50 mM sodium tetraborate buffer (pH 8.3) containing 300 mM NaCl and 5 mM hippuryl-L-histidyl-L-leucine (Sigma Chemical Co., St. Louis, Mo.). ACE (2 mU, EC 3.4.15.1, 100 mU/mL, Sigma) was added, and the reaction mixture was incubated at 37° C. for 35 min. The reaction was terminated by the addition of 250 μL of 1 M HCl. The hippuric acid formed by the action of ACE was extracted with ethyl acetate, and the amount of hippuric acid was measured spectrophotometrically at 228 nm after removal of ethyl acetate by heat evaporation. The ACE inhibiting percentage was calculated by the following equation: Inhibiting percentage=(A−B)/(A−C)×100%, where A is the absorbance at 228 nm of hippuric acid free of sample, B is the absorbance at 228 nm of hippuric acid with sample, and C is the absorbance at 228 nm of hippuric acid free of ACE and sample. The concentration of ACE inhibitor was defined as that needed to inhibit 50% of the ACE activity (IC50).

Two groups of fractions eluted from 13-16 min (the pooled mixture named as Fraction A) and from 32-33 min (the pooled mixture named as Fraction B) exhibited higher ACE inhibitory activity (over 80%). Fraction A and Fraction B were collected from several more HPLC runs for further determination of antihypertensive activity in vivo by measuring the change of blood pressure in SHRs after oral administration of these two fractions as described in Example 1.

Figure 3:
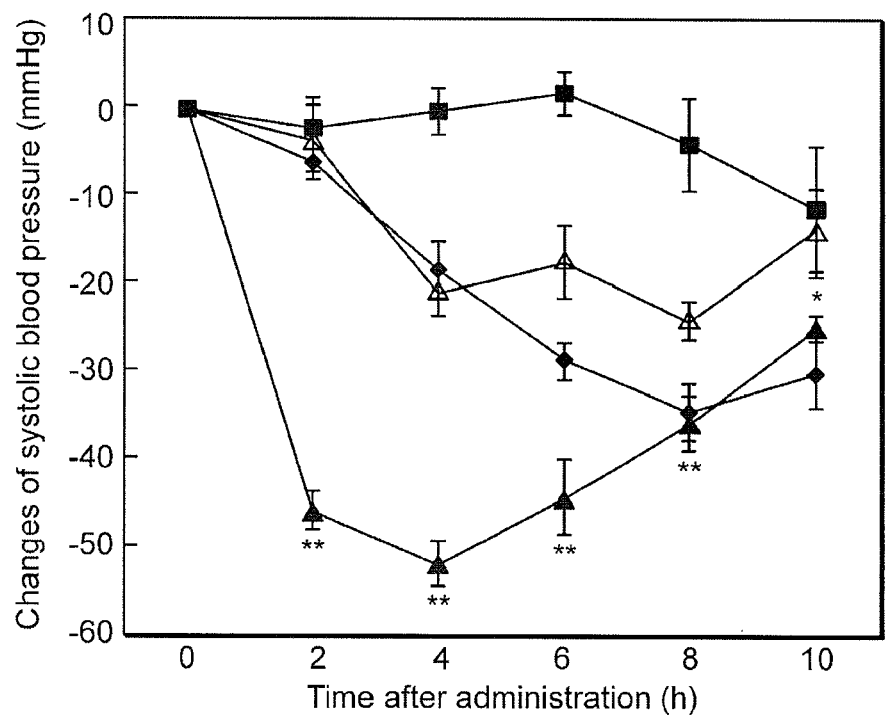
FIG. 3 is a diagram showing the change of SBP in SHRs measured during the first 10 h after a single oral administration of Fraction A and Fraction B obtained in Example 2. The treatment groups were fed with a dose of 35 mg/kg BW of supernatant powder of the fermented dairy product of Example 1 (n=9, ♦), with a dose of 1 mg/kg BW of Fraction A (n=9, ▲), or with a dose of 1 mg/kg BW of Fraction B (n=6, Δ). The control group was fed with a dose of 35 mg/kg BW of supernatant powder of milk (n=6, ■). Data are shown as mean±S.E. Asterisks indicate the level of significant difference from the control at each time interval: * indicating $P<0.05$ and ** indicating $P<0.01$.
Figure 4:
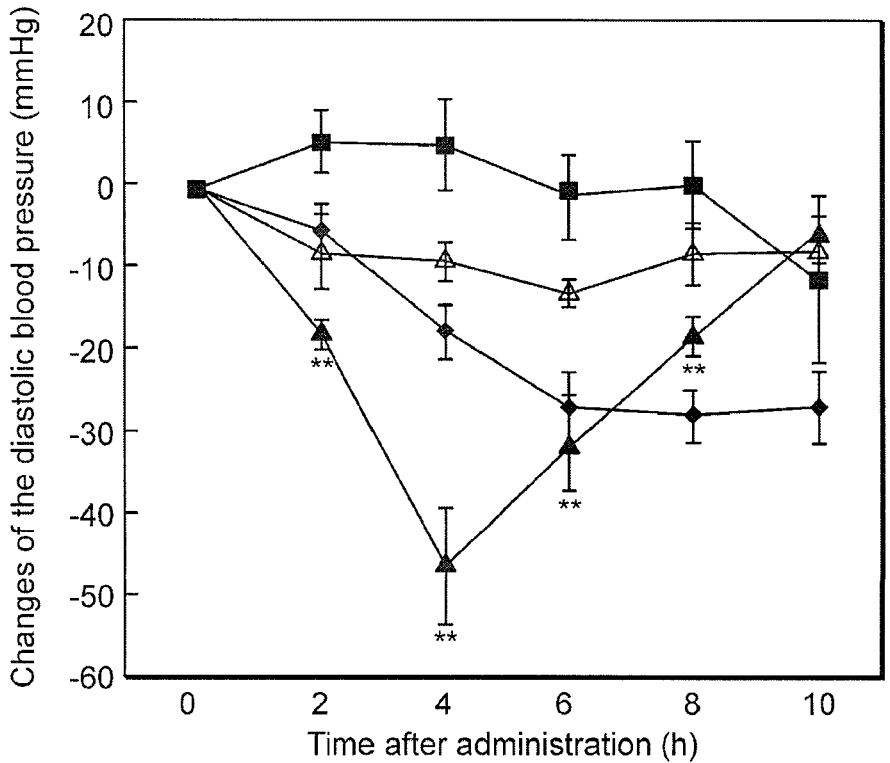
FIG. 4 is a diagram showing the change of DBP in SHRs measured during the first 10 h after a single oral administration of Fraction A and Fraction B obtained in Example 2. The treatment groups were fed with a dose of 35 mg/kg BW of supernatant powder of the fermented dairy product of Example 1 (n=9, ♦), with a dose of 1 mg/kg BW of Fraction A (n=9, ▲), or with a dose of 1 mg/kg BW of Fraction B (n=6, Δ). The control group was fed with a dose of 35 mg/kg BW of supernatant powder of milk (n=6, ■). Data are shown as mean±S.E. Asterisks indicate the level of significant difference from the control at each time interval: ** indicating $P<0.01$.

The change of SBP and DBP in SHRs during the first 10 h after administration of a dose of 1 mg/kg BW of Fraction A and Fraction B were shown in FIG. 3 and FIG. 4. The change of blood pressure in SHRs administered with the supernatant of the fermented dairy product and of milk was used as references. Fraction A exhibited potent antihypertensive activity with the maximal SBP decrease up to 52.5±2.4 mmHg and DBP decrease up to 45.9±7.0 mmHg at 4 h.

Fraction B exhibited high ACE inhibitory activity in vitro but low antihypertensive activity in vivo. Therefore, Fraction A was chosen for further identification of the peptides effective for reducing blood pressure.

Example 3

Identification of Antihypertensive Peptides and Synthesis of the Peptide of Interest Fraction A, which exhibited significant antihypertensive activity in vivo, was collected from 20 HPLC runs and used for further purification by RP-HPLC. The elution condition for the further purification was different from the aforementioned. Solvent A' (1% trifluoroacetic acid in 50% acetonitrile) and solvent B (ddH2O) were used as mobile phase. The peptides were eluted by a gradient from 100% solvent B to 20% solvent B during 0-10 min, 20% solvent B to 30% solvent B during 10-60 min at a flow rate of 1 mL/min.

Figure 5:
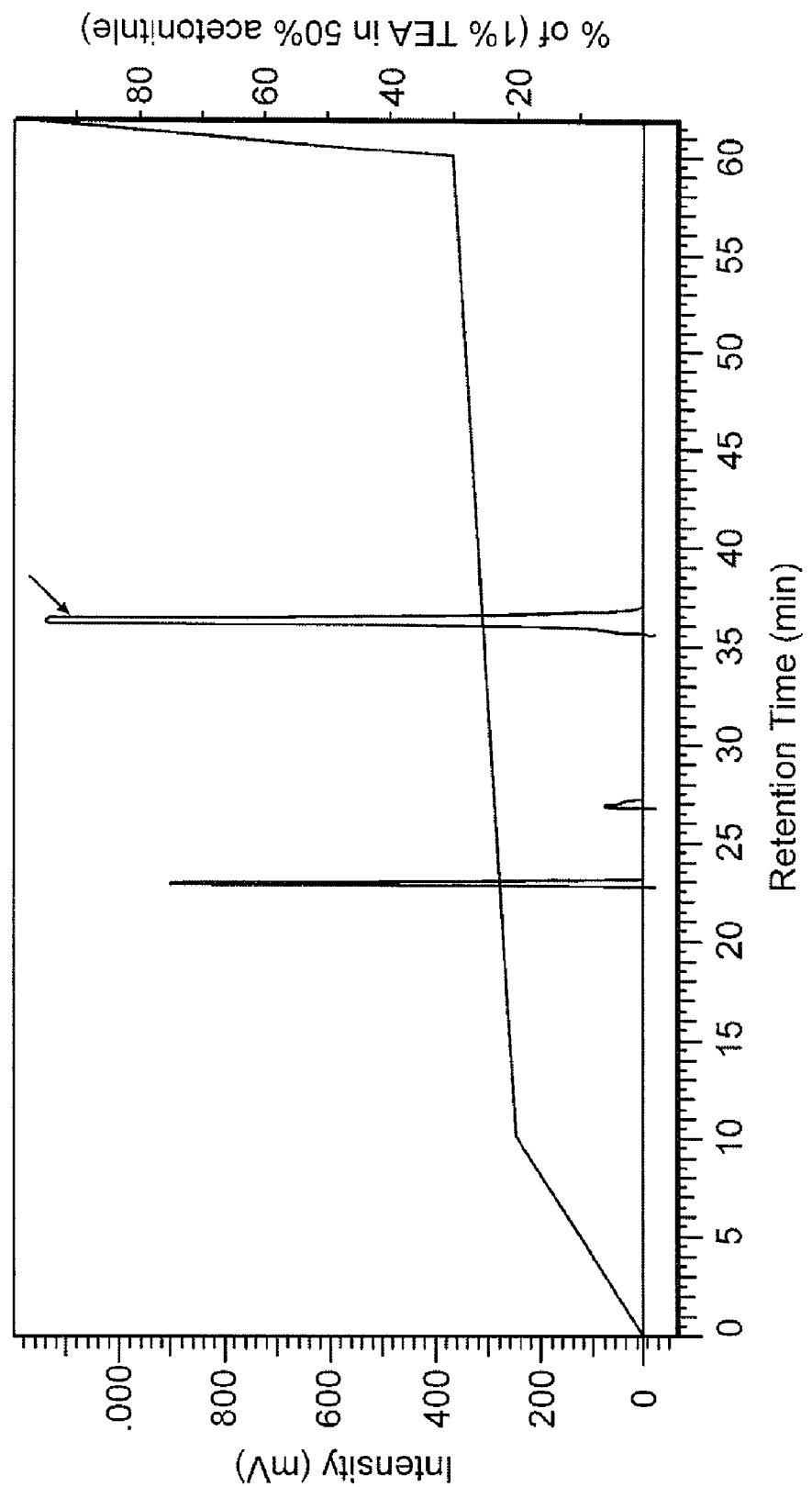
FIG. 5 is an HPLC spectrum showing the fractionation of Fraction A obtained in Example 2 by RP-HPLC. The two major peaks were collected for further identification by a 2-D electrophoresis system. The arrow indicates the peak containing the peptide with the value of isoelectric point (pI) being about 10 and the molecular weight (Mw) being about 2 kDa.

The two major peaks resulted from the further purification were shown in FIG. 5. The elution of each major peak was further separated and characterized using 2-D electrophoresis system (PROTEAN IEF for the first-dimension and Mini-PROTEAN 3 for the second-dimension, Bio-Rad Laboratories, Inc., USA). Results show that there was a predominant spot with pI≈10 and Mw≈2 kD in the elution at 36 min of retention time. In the other major peak, the peptides could not be clearly separated. Therefore, only the spot with pI≈10 and Mw≈2 kD was subjected to amino acid sequencing by a protein sequencer (Perkin Elmer ABI Model 491, USA).

The sequence of the identified peptide derived from Fraction A consisted of 19 amino acids: Val-Leu-Ser-Leu-Ser-Gln-Pro-Lys-Val-Leu-Pro-Val-Pro-Gln-Lys-Ala-Val-Pro-Gln (SEQ ID NO: 1). This peptide was found in the primary structure of β-casein and seemed to be liberated from casein molecule during fermentation. The amino acid sequence of SEQ ID NO: 1 was then synthesized by Protech Technology Enterprise Co., Ltd. (Taipei, Taiwan) and tested for its antihypertensive activity in SHRs in the following example.

Example 4

Confirmation of the Antihypertensive Activity of the Peptide of Interest

Figure 6:
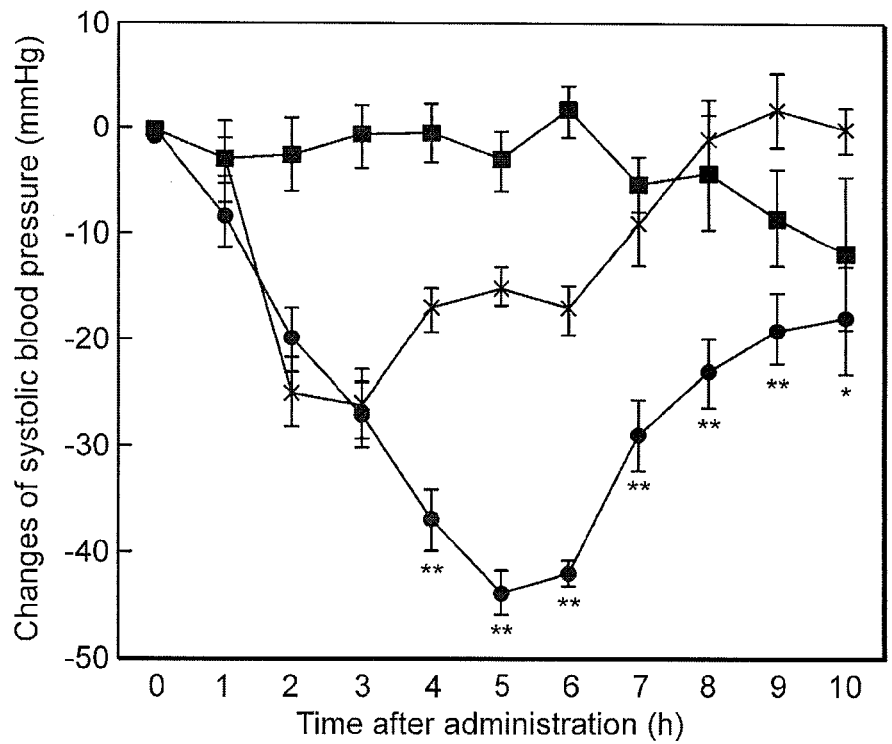
FIG. 6 is a diagram showing the change of SBP in SHRs measured during the first 10 h after a single oral administration of the synthetic antihypertensive peptide Val-Leu-Ser-Leu-Ser-Gln-Pro-Lys-Val-Leu-Pro-Val-Pro-Gln-Lys-Ala-Val-Pro-Gln (SEQ ID NO: 1) identified from Fraction A and the tripeptide Val-Pro-Pro (SEQ ID NO: 2). The treatment groups were fed with a dose of 1 mg/kg BW of Val-Leu-Ser-Leu-Ser-Gln-Pro-Lys-Val-Leu-Pro-Val-Pro-Gln-Lys-Ala-Val-Pro-Gln (SEQ ID NO: 1) (n=9, ●) or with a dose of 1 mg/kg BW of Val-Pro-Pro (SEQ ID NO: 2) (n=6, x). The control group was fed with a dose of 35 mg/kg BW of supernatant powder of milk (n=6, ■). Data are shown as mean±S.E. Asterisks indicate the level of significant difference from VPP at each time interval: * indicating $P<0.05$ and ** indicating $P<0.01$.
Figure 7:
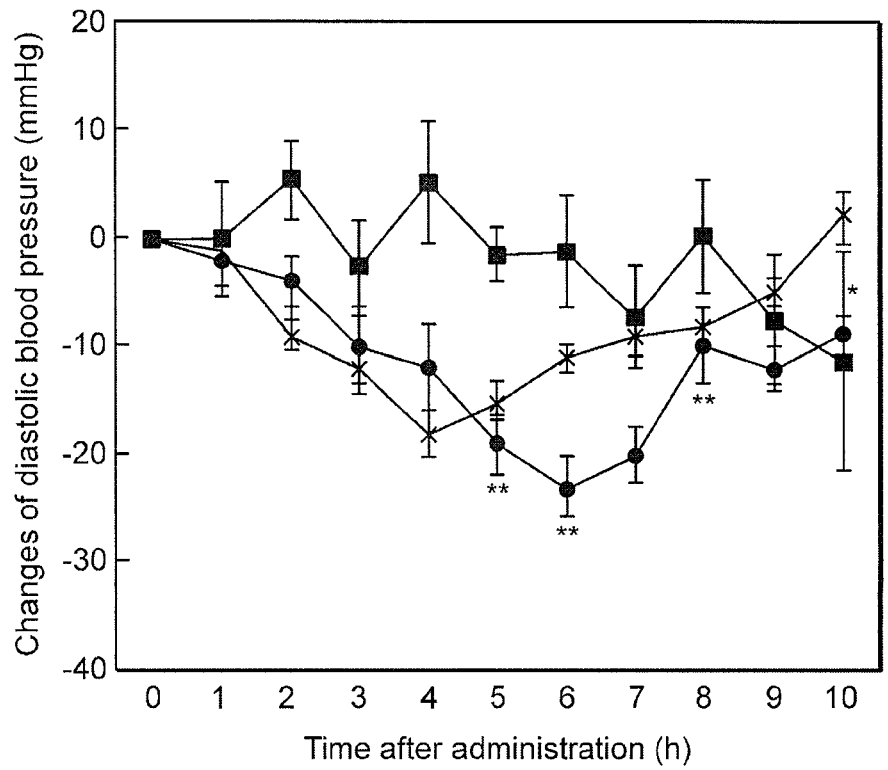
FIG. 7 is a diagram showing the change of DBP in SHRs measured during the first 10 h after a single oral administration of the synthetic antihypertensive peptide Val-Leu-Ser-Leu-Ser-Gln-Pro-Lys-Val-Leu-Pro-Val-Pro-Gln-Lys-Ala-Val-Pro-Gln (SEQ ID NO: 1) identified from Fraction A and the tripeptide Val-Pro-Pro (SEQ ID NO: 2). The treatment groups were fed with a dose of 1 mg/kg BW of Val-Leu-Ser-Leu-Ser-Gln-Pro-Lys-Val-Leu-Pro-Val-Pro-Gln-Lys-Ala-Val-Pro-Gln (SEQ ID NO: 1) (n=9, ●) or with a dose of 1 mg/kg BW of Val-Pro-Pro (SEQ ID NO: 2) (n=6, x). The control group was fed with a dose of 35 mg/kg BW of supernatant powder of milk (n=6, ■). Data are shown as mean±S.E. Asterisks indicate the level of significant difference from Val-Pro-Pro (SEQ ID NO: 2) at each time interval: * indicating $P<0.05$ and ** indicating $P<0.01$.

The synthetic peptide with the same sequence as the identified peptide of SEQ ID NO: 1, was used to confirm the antihypertensive effect in vivo by the same procedure as described in Example 1. As shown in FIG. 6 and FIG. 7, a single oral administration of this peptide to SHRs with a dose of 1 mg/kg BW exhibited a potent antihypertensive effect both in SBP and DBP. In addition, the tripeptide VPP was synthesized and tested in SHRs as the positive control group. Val-Pro-Pro (SEQ ID NO: 2) derived from β-casein has been reported to decrease SBP in SHRs with a dose of 1.6 mg/kg BW by 20 mmHg at 6 h after oral administration (Nakamura et al., 1995, *J. Dairy Sci.* 78: 1253-1257; Nakamura et al., 1995, *J. Dairy Sci.* 78: 777-783). Besides, VPP is labeled as one of the two key components in Calpis sour milk drink, a popular functional food on market for controlling blood pressure. As shown in FIG. 6 and FIG. 7, Val-Pro-Pro (SEQ ID NO: 2) had a maximal decrease of 26.3±3.2 mmHg in SBP and 18.0±2.1 mmHg in DBP at 4 h after oral administration with a dose of 1 mg/kg BW. As to the identified peptide of 19 a.a.: Val-Leu-Ser-Leu-Ser-Gln-Pro-Lys-Val-Leu-Pro-Val-Pro-Gln-Lys-Ala-Val-Pro-Gln (SEQ ID NO: 1), the maximal decrease of SBP and DBP were up to 44.0±2.1 mmHg at 5 h and 23.0±2.9 mmHg at 6 h, respectively. These data show that the peptide identified in the Example 3 had a potent antihypertensive effect in vivo.

Figure 8:
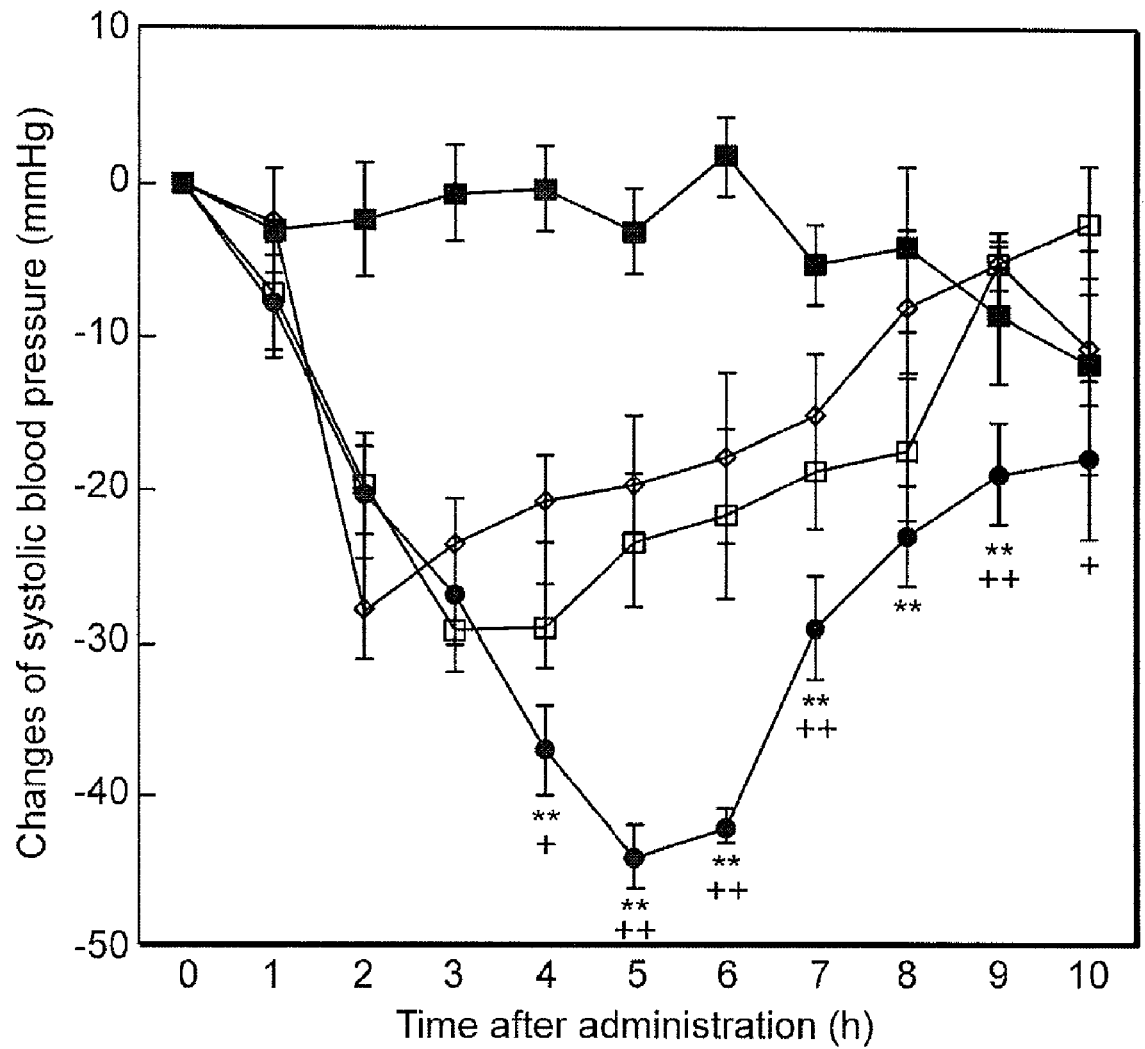
FIG. 8 is a diagram showing the change of SBP in SHRs measured during the first 10 h after a single oral administration of synthetic peptides Val-Leu-Ser-Leu-Ser-Gln-Pro-Lys-Val-Leu-Pro-Val-Pro-Gln-Lys-Ala-Val-Pro-Gln (SEQ ID NO: 1), Val-Pro-Pro (SEQ ID NO: 2), Lys-Val-Leu-Pro-Val-Pro (SEQ ID NO: 3), and Lys-Val-Leu-Pro-Val-Pro-Gln (SEQ ID NO: 4). The treatment groups were fed with a dose of 1 mg/kg BW of Val-Leu-Ser-Leu-Ser-Gln-Pro-Lys-Val-Leu-Pro-Val-Pro-Gln-Lys-Ala-Val-Pro-Gln (SEQ ID NO: 1) (n=9, ●), with a dose of 1 mg/kg of Lys-Val-Leu-Pro-Val-Pro (SEQ ID NO: 3) (n=6, □), or with a dose of 1 mg/kg of, and Lys-Val-Leu-Pro-Val-Pro-Gln (SEQ ID NO: 4) (n=6, □). The control group was fed with a dose of 35 mg/kg BW of supernatant powder of milk (n=6, ■). Data are shown as mean±S.E. Asterisks indicate the level of significant difference from Val-Pro-Pro (SEQ ID NO: 2), Lys-Val-Leu-Pro-Val-Pro (SEQ ID NO: 3) at each time interval: * indicating $P<0.05$ and ** indicating $P<0.01$. Plus signs indicate the level of significant difference from Lys-Val-Leu-Pro-Val-Pro-Gln (SEQ ID NO: 4) at each time interval: + indicating $P<0.05$ and ++ indicating $P<0.01$.
Figure 9:
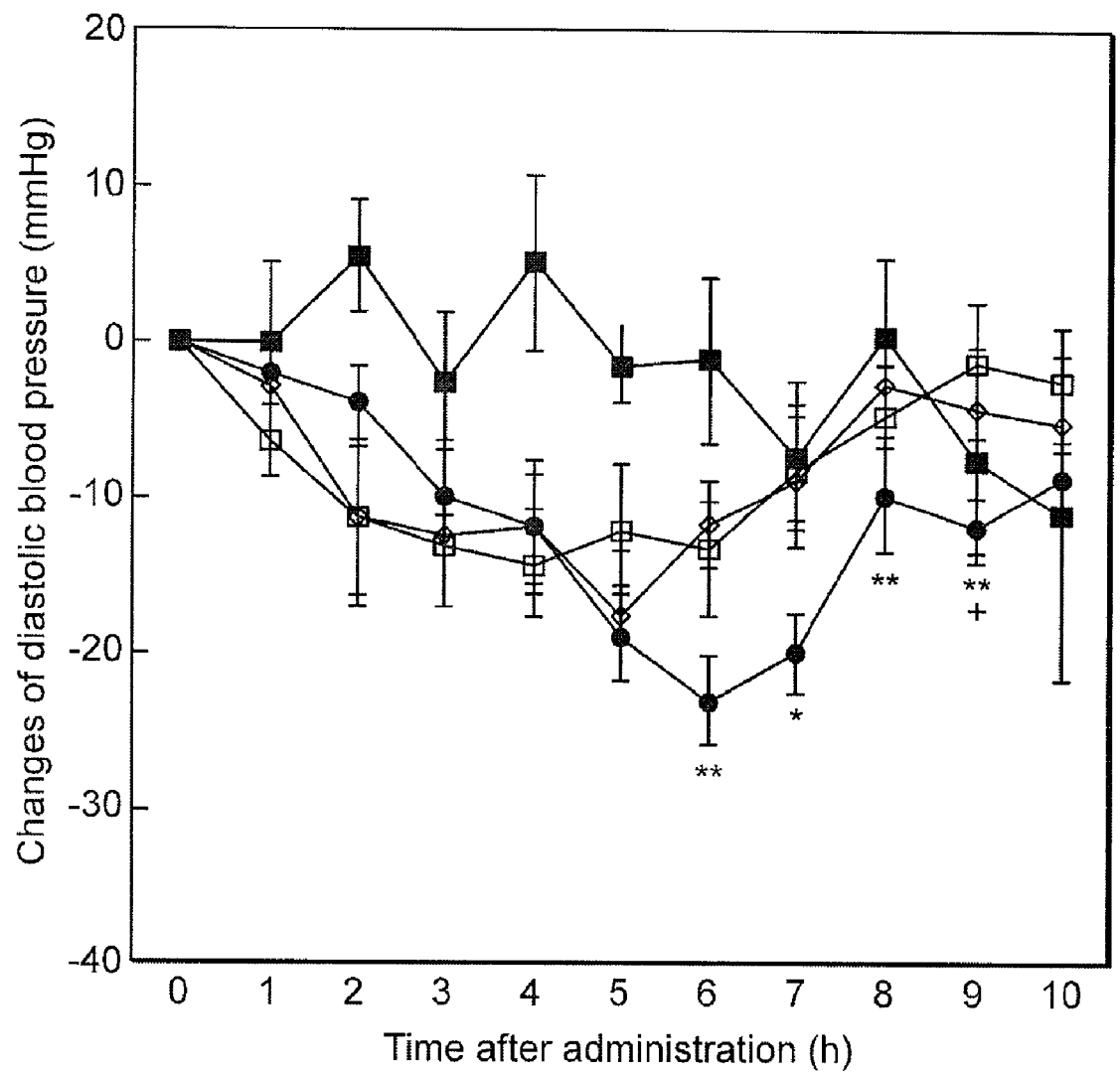
FIG. 9 is a diagram showing the change of DBP in SHRs measured during the first 10 h after a single oral administration of synthetic peptides Val-Leu-Ser-Leu-Ser-Gln-Pro-Lys-Val-Leu-Pro-Val-Pro-Gln-Lys-Ala-Val-Pro-Gln (SEQ ID NO: 1), Val-Pro-Pro (SEQ ID NO: 2), Lys-Val-Leu-Pro-Val-Pro (SEQ ID NO: 3), and Lys-Val-Leu-Pro-Val-Pro-Gln (SEQ ID NO: 4). The treatment groups were fed with a dose of 1 mg/kg BW of Val-Leu-Ser-Leu-Ser-Gln-Pro-Lys-Val-Leu-Pro-Val-Pro-Gln-Lys-Ala-Val-Pro-Gln (SEQ ID NO: 1) (n=9, ●), with a dose of 1 mg/kg of Val-Pro-Pro (SEQ ID NO: 2), Lys-Val-Leu-Pro-Val-Pro (SEQ ID NO: 3) (n=6, □), or with a dose of 1 mg/kg of Lys-Val-Leu-Pro-Val-Pro-Gln (SEQ ID NO: 4) (n=6, □). The control group was fed with a dose of 35 mg/kg BW of supernatant powder of milk (n=6, ●). Data are shown as mean±S.E. Asterisks indicate the level of significant difference from Lys-Val-Leu-Pro-Val-Pro (SEQ ID NO: 3) at each time interval: * indicating $P<0.05$ and ** indicating $P<0.01$. Plus signs indicate the level of significant difference from and Lys-Val-Leu-Pro-Val-Pro-Gln (SEQ ID NO: 4) at each time interval: + indicating $P<0.05$ and ++ indicating $P<0.01$.
Figure 10:
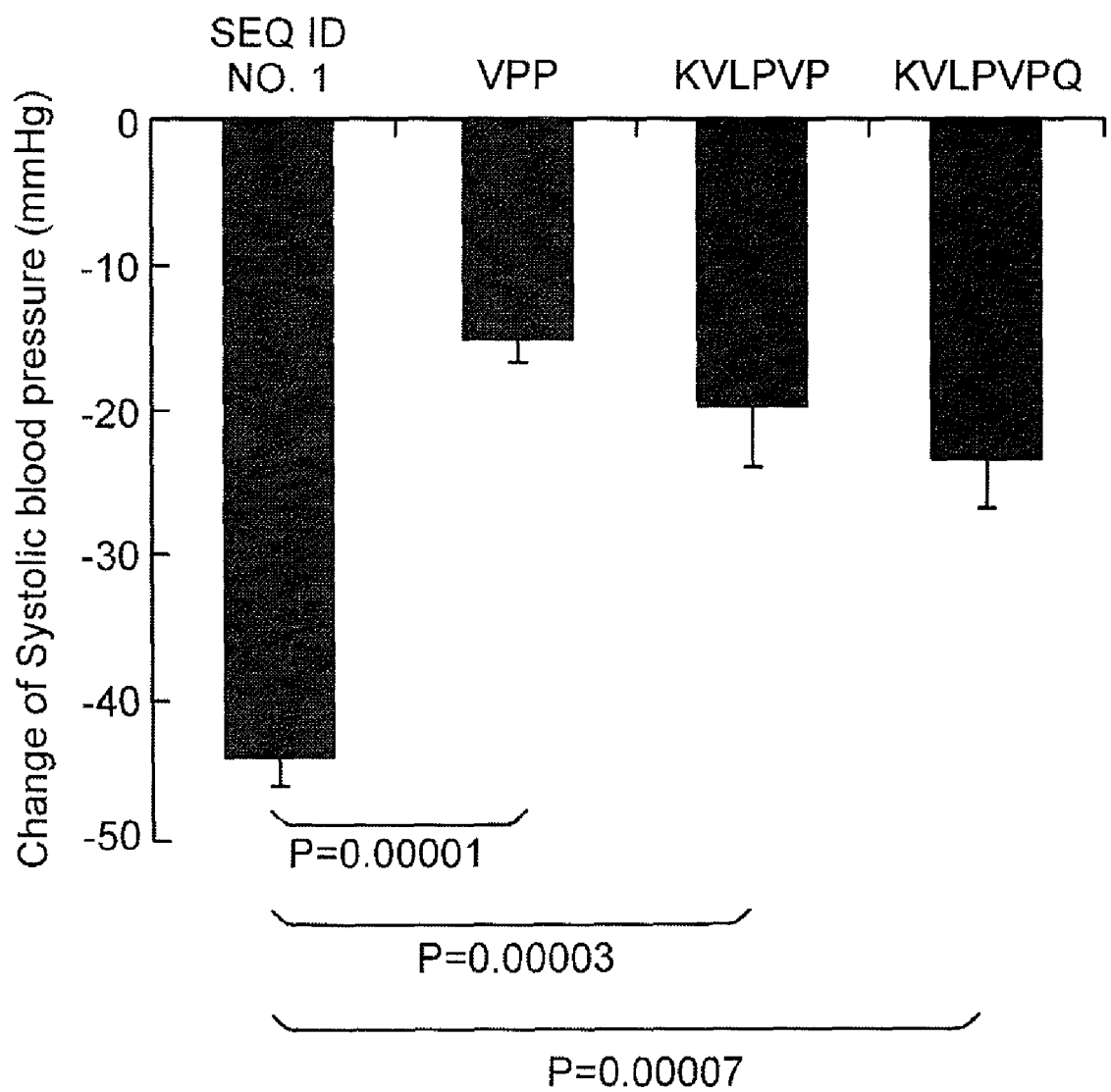
FIG. 10 is a diagram showing the significant differences in SBP change in SHRs between the synthetic peptide Val-Leu-Ser-Leu-Ser-Gln-Pro-Lys-Val-Leu-Pro-Val-Pro-Gln-Lys-Ala-Val-Pro-Gln (SEQ ID NO: 1) and the other peptides, Val-Pro-Pro (SEQ ID NO: 2), Lys-Val-Leu-Pro-Val-Pro (SEQ ID NO: 3) and Lys-Val-Leu-Pro-Val-Pro-Gln (SEQ ID NO: 4), measured at 5 h after a single oral administration of the respective peptides. The treatment groups were all fed at the same dosage of 1 mg/kg BW. Data are shown as mean±S.E. The P values between two groups are shown.

In 1996, Maeno et al. reported that two peptides, Lys-Val-Leu-Pro-Val-Pro (SEQ ID NO: 3) and Lys-Val-Leu-Pro-Val-Pro-Gln (SEQ ID NO: 4), derived from the casein hydrolysate exhibited antihypertensive activity in SHRs (Maeno et al., 1996, ut supra). According to Maeno et al., Lys-Val-Leu-Pro-Val-Pro-Gln (SEQ ID NO: 4) decreased SBP up to 31.5±5.6 mmHg at 6 h after a single oral administration of 2 mg/kg BW. Since our identified peptide of 19 a.a., Val-Leu-Ser-Leu-Ser-Gln-Pro-Lys-Val-Leu-Pro-Val-Pro-Gln-Lys-Ala-Val-Pro-Gln (SEQ ID NO: 1), contained both of the sequences Lys-Val-Leu-Pro-Val-Pro (SEQ ID NO: 3) and Lys-Val-Leu-Pro-Val-Pro-Gln (SEQ ID NO: 4), it was compared with these two peptides (synthetic) for their antihypertensive activities at the same dosage of 1 mg/kg BW. As shown in FIG. 8 and FIG. 9, for the 19 a.a. peptide, the maximal decrease in SBP and DBP were up to 44.0±2.1 mmHg at 5 h and 23.0±2.9 mmHg at 6 h, respectively. However, for Lys-Val-Leu-Pro-Val-Pro (SEQ ID NO: 3), the maximal decrease in SBP and DBP were up to 27.8±3.3 mmHg at 2 h and 17.5±4.2 mmHg at 5 h, respectively. For Lys-Val-Leu-Pro-Val-Pro-Gln (SEQ ID NO: 4), the maximal decreases in SBP and DBP were up to 29.2±4.0 mmHg at 3 h and 14.4±3.2 mmHg at 4 h, respectively. FIG. 10 shows that Val-Leu-Ser-Leu-Ser-Gln-Pro-Lys-Val-Leu-Pro-Val-Pro-Gln-Lys-Ala-Val-Pro-Gln (SEQ ID NO: 1) exhibited extremely significantly higher antihypertensive activity than Val-Pro-Pro (SEQ ID NO: 2) (P=0.00001), Lys-Val-Leu-Pro-Val-Pro (SEQ ID NO: 3) (P=0.00003) and Lys-Val-Leu-Pro-Val-Pro-Gln (SEQ ID NO: 4) (P=0.00007).

Furthermore, to verify that the high antihypertensive activity exhibited in vivo by our 19-a.a. peptide was not provided by either Lys-Val-Leu-Pro-Val-Pro (SEQ ID NO: 3) or Lys-Val-Leu-Pro-Val-Pro-Gln (SEQ ID NO: 4) as a result of digestion, the synthesized peptide Val-Leu-Ser-Leu-Ser-Gln-Pro-Lys-Val-Leu-Pro-Val-Pro-Gln-Lys-Ala-Val-Pro-Gln (SEQ ID NO: 1) was digested under simulated gastro-intestinal condition as described by Alting et al. in *Diabetes Care* 20: 875-880 (1997). Briefly, the peptide was digested with a pepsin solution (pH 2.5) (EC 3.4.23.1; 1:10000; Sigma, USA) for 1.5 h at 37° C., followed by digestion with Corolase PP (pH 7.5) (pancreatic protease; Rohm, Darmstadt, German) for 2.5 h at 37° C. To remove the enzyme added, the digested peptide solution was filtered through a 3 kDa cut-off centrifugal filter (Microcon YM-3, 3 kDa NMWL, Millipore Co., USA) by centrifugation at 1,000×g for 10 min. The filtrate was then used in the analysis for peptide fragments by MALDI-TOF-MS (matrix-assisted laser desorption ionization-time of flight mass spectrometry).

Figure 11:
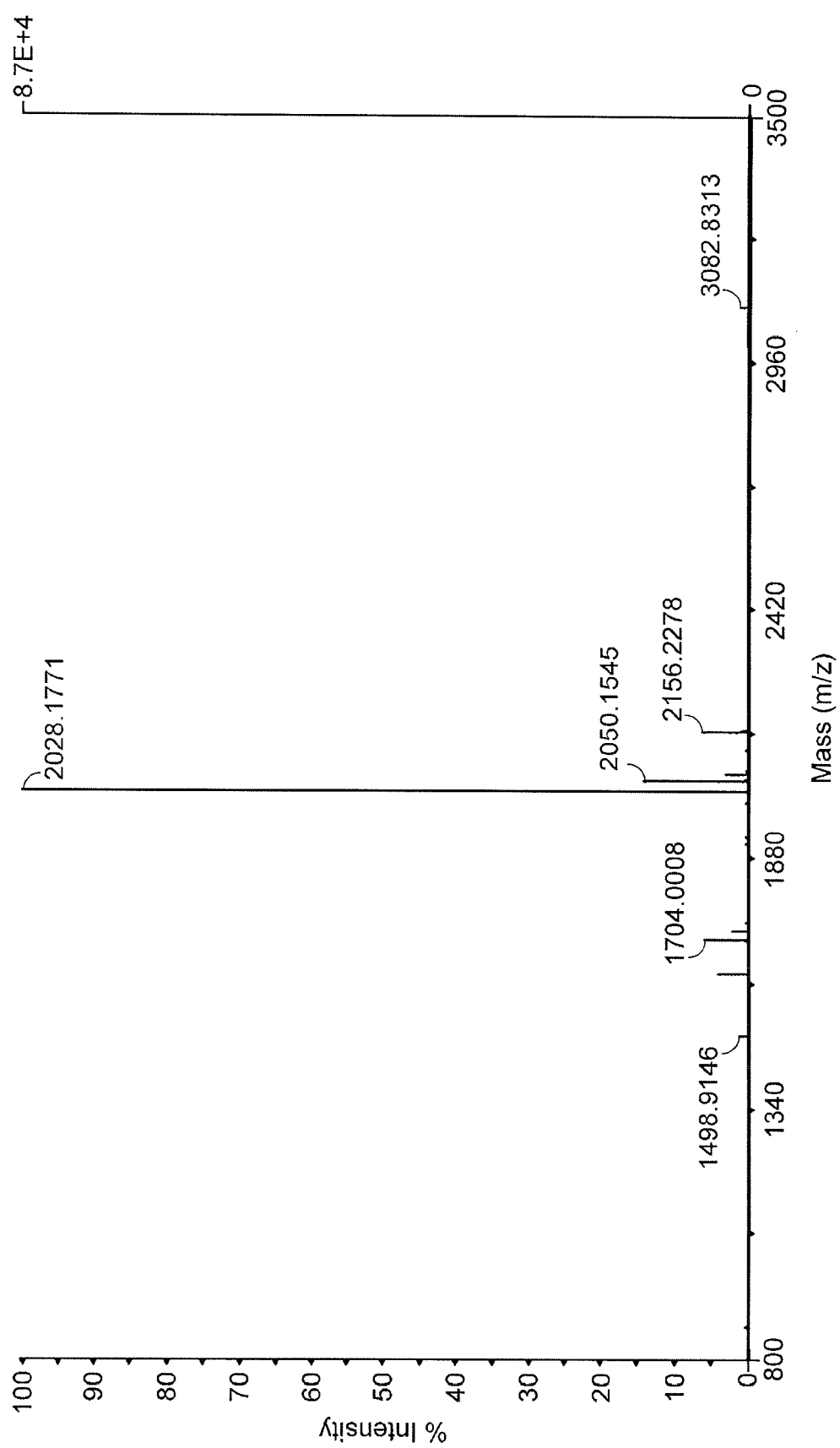
FIG. 11 is a MALDI-TOF-MS spectrum of the synthetic peptide Val-Leu-Ser-Leu-Ser-Gln-Pro-Lys-Val-Leu-Pro-Val-Pro-Gln-Lys-Ala-Val-Pro-Gln (SEQ ID NO: 1).
Figure 12:
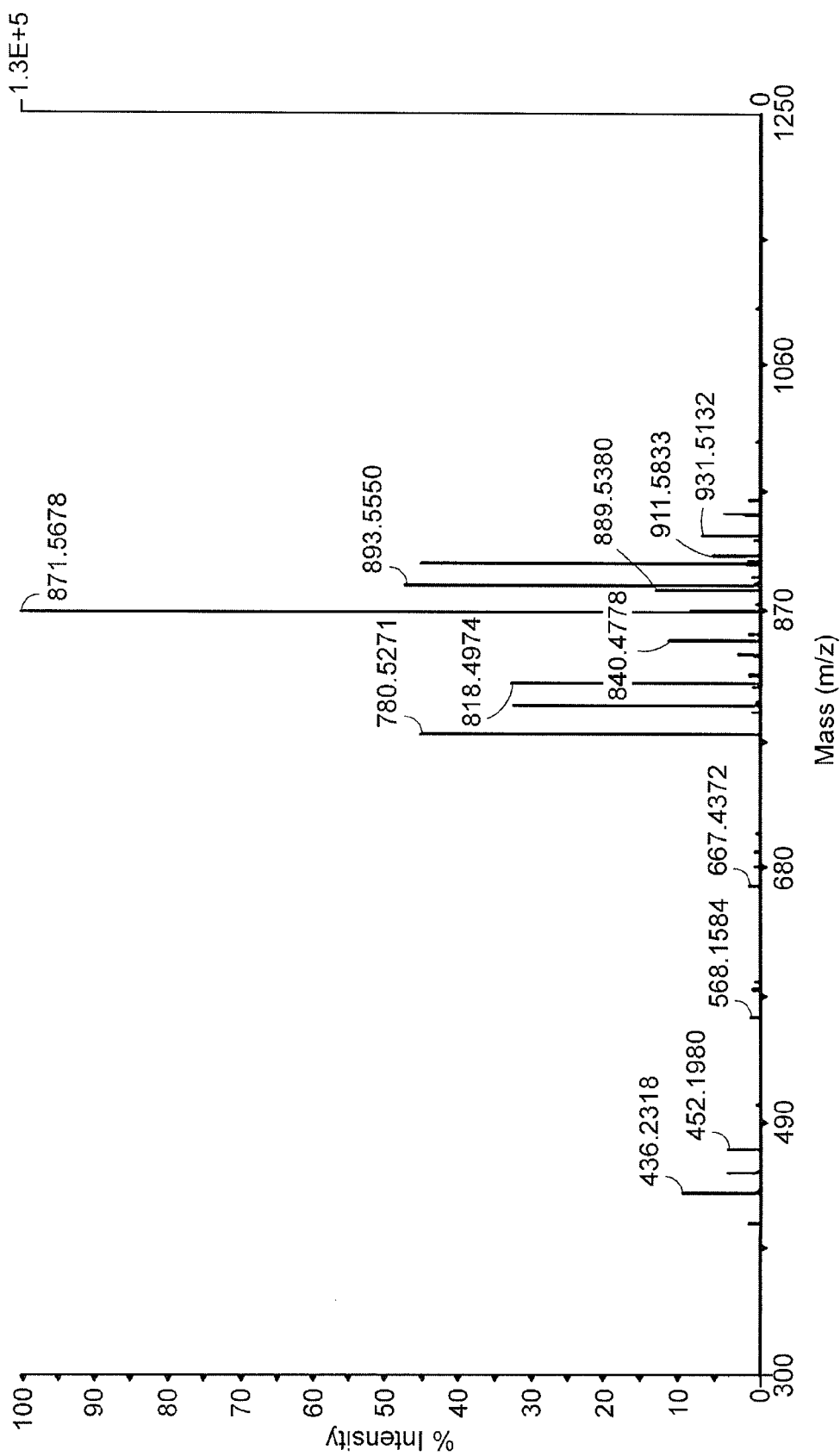
FIG. 12 is a MALDI-TOF-MS spectrum showing peptide fragments derived from the synthetic peptide Val-Leu-Ser-Leu-Ser-Gln-Pro-Lys-Val-Leu-Pro-Val-Pro-Gln-Lys-Ala-Val-Pro-Gln (SEQ ID NO: 1) after simulated gastro-intestinal digestion.

As shown in FIG. 11, FIG. 12 and Table 1 below, the peptide fragments derived from the 19-a.a. peptide, Val-Leu-Ser-Leu-Ser-Gln-Pro-Lys-Val-Leu-Pro-Val-Pro-Gln-Lys-Ala-Val-Pro-Gln (SEQ ID NO: 1) as identified in Example 3 after simulating gastro-intestinal digestion did not contain Lys-Val-Leu-Pro-Val-Pro (SEQ ID NO: 3) or Lys-Val-Leu-Pro-Val-Pro-Gln (SEQ ID NO: 4). Furthermore, the 19-a.a. peptide, Val-Leu-Ser-Leu-Ser-Gln-Pro-Lys-Val-Leu-Pro-Val-Pro-Gln-Lys-Ala-Val-Pro-Gln (SEQ ID NO: 1) provided an significantly higher antihypertensive activity than either of the known peptides, Lys-Val-Leu-Pro-Val-Pro (SEQ ID NO: 3) and Lys-Val-Leu-Pro-Val-Pro-Gln (SEQ ID NO: 4).

Table 1, amino acid sequences of peptide fragments derived from the synthetic peptide Val-Leu-Ser-Leu-Ser-Gln-Pro-Lys-Val-Leu-Pro-Val-Pro-Gln-Lys-Ala-Val-Pro-Gln (VLSLSQPKVLPVPQKAVPQ) of SEQ ID NO: 1 after simulated gastro-intestinal digestion.

| No. | m/z (mi) | m/z (av) | Start | End | Missed Cleavages | Sequence |
|---|---|---|---|---|---|---|
| 1 | 414.2347 | 414.4845 | 16 | 19 | 0 | (K) AVPQ (-) (SEQ ID NO: 5) |
| 1 | 780.4978 | 780.9917 | 9 | 15 | 0 | (K) VLPVPQK (A) (SEQ ID NO: 6) |
| 1 | 871.5247 | 872.0586 | 1 | 8 | 0 | (-) VLSLSQPK (V) (SEQ ID NO: 7) |
| 1 | 1175.7147 | 1176.4534 | 9 | 19 | 1 | (K) VLPVPQKAVPQ (-) (SEQ ID NO: 8) |
| 1 | 1633.0047 | 1634.0276 | 1 | 15 | 1 | (-) VLSLSQPKVLPVPQK (A) (SEQ ID NO: 9) |
| 1 | 2028.2216 | 2029.4893 | 1 | 19 | 2 | (-) VLSLSQPKVLPVPQKAVPQ (SEQ ID NO: 1) |

Statistical Analysis:

All data in the above examples were analyzed using statistical software package SAS version 9.1 (SAS Institute, Cary, N.C.) and the significances of differences among groups were evaluated using the Mann Whitney U test. A P value<0.05 was considered as significant.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An isolated antihypertensive peptide comprising the amino acid sequence of SEQ ID NO:1, wherein said peptide has 50 amino acids or less.

2. The antihypertensive peptide of claim 1 wherein the antihypertensive peptide consists of the amino acid sequence of SEQ ID NO:1.

3. A pharmaceutical composition comprising the antihypertensive peptide of claim 1 and a pharmaceutically acceptable carrier.

4. The pharmaceutical composition of claim 3, wherein the composition is for oral administration.

5. The pharmaceutical composition of claim 3, wherein the antihypertensive peptide consists of the amino acid sequence of SEQ ID NO:1.

6. A food product comprising the antihypertensive peptide of claim 1 and a food substance.

7. The food product of claim 6, wherein the food product is a fermented dairy product.

8. The food product of claim 6, wherein the antihypertensive peptide consists of the amino acid sequence of SEQ ID NO:1.

9. A method for treating hypertension, comprising administering to a subject in need thereof an effective amount of a composition comprising the antihypertensive peptide of claim 1.

10. The method of claim 9 wherein the antihypertensive peptide consists of the amino acid sequence of SEQ ID NO:1.

11. The method of claim 9, wherein the composition is a fermented dairy product.

* * * * *